US012176078B2

(12) United States Patent
Reynier

(10) Patent No.: US 12,176,078 B2
(45) Date of Patent: Dec. 24, 2024

(54) SYSTEM AND METHOD FOR COMMUNICATING HEALTH DATA IN A HEALTHCARE ENVIRONMENT

(71) Applicant: Fresenius Vial SAS, Brézins (FR)

(72) Inventor: Christophe Reynier, Chirens (FR)

(73) Assignee: Fresenius Vial SAS, Brézins (FR)

( * ) Notice: Subject to any disclaimer, the term of this patent is extended or adjusted under 35 U.S.C. 154(b) by 0 days.

(21) Appl. No.: 16/618,614

(22) PCT Filed: Sep. 5, 2018

(86) PCT No.: PCT/EP2018/073798
§ 371 (c)(1),
(2) Date: Dec. 2, 2019

(87) PCT Pub. No.: WO2019/063249
PCT Pub. Date: Apr. 4, 2019

(65) Prior Publication Data
US 2020/0185068 A1 Jun. 11, 2020

(30) Foreign Application Priority Data
Sep. 27, 2017 (EP) .................................. 17306282

(51) Int. Cl.
*G16H 10/60* (2018.01)
*G16H 40/67* (2018.01)
*G16H 80/00* (2018.01)

(52) U.S. Cl.
CPC .............. *G16H 10/60* (2018.01); *G16H 40/67* (2018.01); *G16H 80/00* (2018.01)

(58) Field of Classification Search
CPC ........ G16H 10/60; G16H 40/67; G16H 80/00; H04L 67/12; H04W 4/38
(Continued)

(56) References Cited

U.S. PATENT DOCUMENTS 6,260,148 B1 * 7/2001 Aggarwal ............. H04L 51/214
726/14
7,085,814 B1 * 8/2006 Gandhi ................... H04L 67/14
709/208
(Continued)

FOREIGN PATENT DOCUMENTS

CN 105681442 6/2016
CN 107018147 8/2017
(Continued)

OTHER PUBLICATIONS

International Search Report and Written Opinion, counterpart International Appl. No. PCT/EP2018/073798 (Oct. 11, 2018) (13 pages).
(Continued)

*Primary Examiner* — Mark Holcomb
(74) *Attorney, Agent, or Firm* — Cook Alex Ltd.

(57) ABSTRACT

A system for communicating health data in a healthcare environment (1) comprises a communication network (4) for communicating health data in the healthcare environment (1), a reporting device (2) for transferring health data via the communication network (4), and a consuming device (3) for receiving health data from the reporting device (2) via a communication channel (41) of the communication network (4). Herein, the consuming device (3), for receiving health data from the reporting device (2), is constituted to send a subscription request message (A1) containing a subscription request to the reporting device (2), and that the reporting device (2) is constituted, upon receiving the subscription request message (A1), to validate the subscription request and to establish the communication channel (41) to transfer health data to the consuming device (3). In this way a system is provided which may allow for an easy connection of a consuming device to a network with the possibility to reduce the data load and to improve a backup handling.

18 Claims, 3 Drawing Sheets

(58) Field of Classification Search
USPC .......................................................... 705/2–4
See application file for complete search history.

(56) References Cited

U.S. PATENT DOCUMENTS

| | | | |
|---|---|---|---|
| 9,071,606 | B2 | 6/2015 | Braun et al. |
| 9,426,151 | B2 | 8/2016 | Richards et al. |
| 9,569,587 | B2 | 2/2017 | Ansari et al. |
| 10,403,394 | B2 | 9/2019 | Ansari et al. |
| 2006/0168043 | A1 | 7/2006 | Eisenberger et al. |
| 2007/0106754 | A1* | 5/2007 | Moore ................... G16H 40/20 707/E17.116 |
| 2008/0288294 | A1* | 11/2008 | Eisenberger ........... G06Q 10/00 705/3 |
| 2011/0077965 | A1* | 3/2011 | Nolte ..................... G06Q 10/10 705/3 |
| 2015/0032809 | A1* | 1/2015 | Xie ..................... H04L 65/1083 709/204 |
| 2016/0373257 | A1* | 12/2016 | Adrangi ................. H04L 9/006 |
| 2017/0215064 | A1 | 7/2017 | Onishi et al. |
| 2017/0347222 | A1* | 11/2017 | Kanter ................... H04W 4/38 |

FOREIGN PATENT DOCUMENTS

| | | |
|---|---|---|
| JP | 2000-287013 | 10/2000 |
| JP | 2008-527519 | 7/2008 |
| JP | 2016-025463 | 2/2016 |
| JP | 2016-509708 | 3/2016 |
| JP | 2017-027499 | 2/2017 |
| WO | WO2014/100557 | 6/2014 |

OTHER PUBLICATIONS

PCD Profile DEC Overview—IHE Wiki, retrieved from "https://wiki.ihe.net/index.php?title=PCD_Profile_DEC_Overview&oldid=103149" (retrieved on Nov. 21, 2017).

Search Report and English-language machine translation, counterpart Japanese App. No. 2020-515226 (Oct. 20, 2022) (29 pages).

Notice of Reasons for Refusal and English-language machine translation, counterpart Japanese App. No. 2020-515226 (Oct. 25, 2022) (6 pages).

Office Action and Search Report (with English-language translation), counterpart Chinese App. No. 201880057791.8 (Oct. 27, 2023) (17 pages).

* cited by examiner

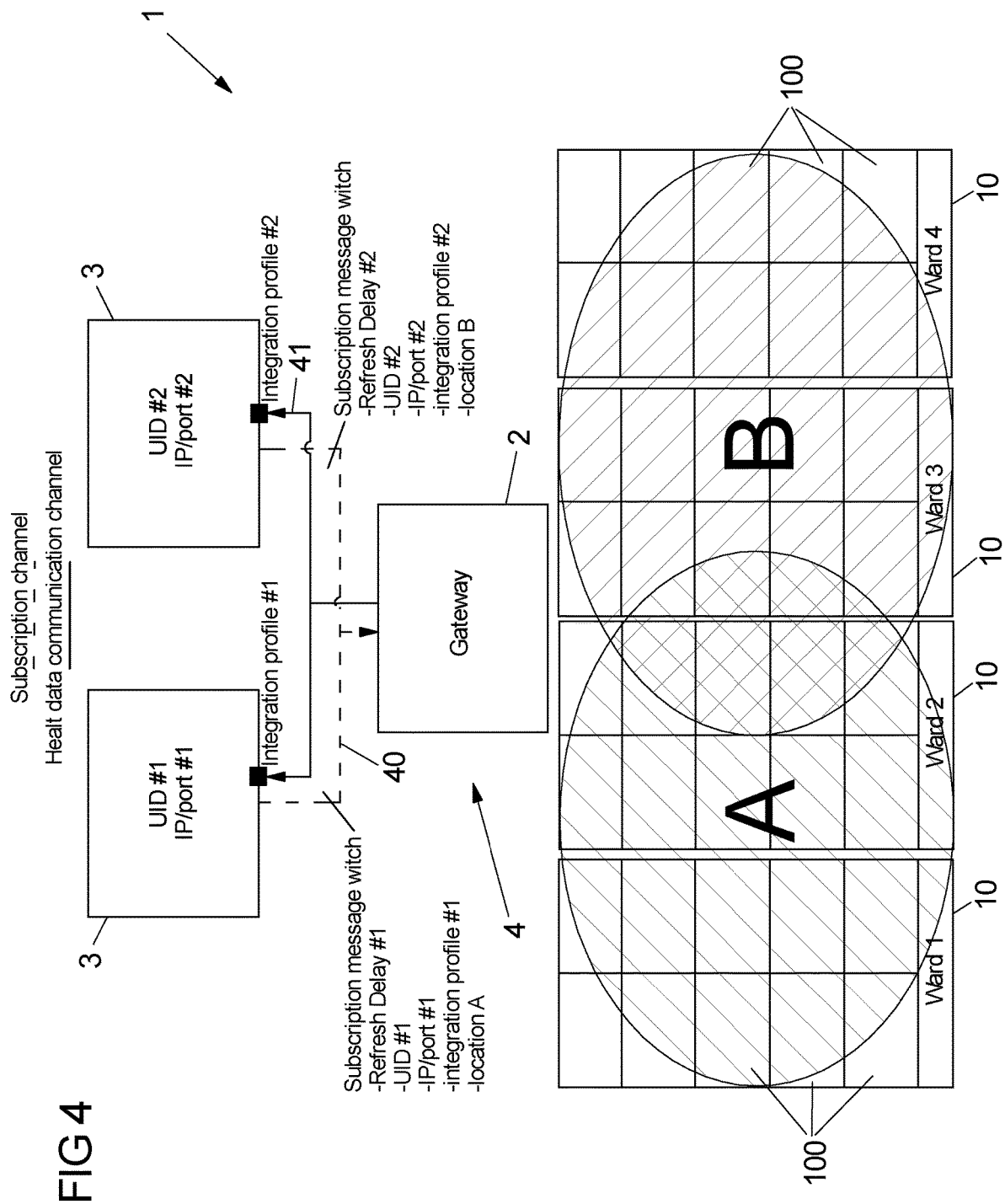

SYSTEM AND METHOD FOR COMMUNICATING HEALTH DATA IN A HEALTHCARE ENVIRONMENT

The present application is a U.S. National Stage of PCT International Patent Application No. PCT/EP2018/073798, filed Sep. 5, 2018, which claims priority to EP application Ser. No. 17/306,282, filed Sep. 27, 2017, both of which are hereby incorporated herein by reference.

The invention relates to a system for communicating health data in a healthcare environment according to the preamble of claim 1 and to a method for communicating health data in a healthcare environment.

A system of this kind comprises a communication network for communicating health data in the healthcare environment. A reporting device in this regard serves for transferring health data via the communication network, and a consuming device serves for receiving health data from the reporting device via a communication channel of the communication network.

Typically, in a healthcare environment such as a hospital a multiplicity of patient care devices, for example infusion devices for administering medication to patients, are operated at different locations in the healthcare environment, for example in different departments (such as general wards, intensive care units, emergency departments and the like) and in different rooms of the different departments at for example the bedside of different patients. Such patient care devices are typically run independently and produce data, for example relating to infusion operations that have been carried out or are ongoing, which at least to some extent shall be transferred as health data to for example a hospital information system (HIS).

Within a hospital communication network, patient care devices are typically connected to a gateway device, which for example pre-processes health data received from the patient care devices for transferring the health data on to the hospital information system.

The hospital information system generally is to be understood as a set of information processing systems for collecting, processing and distributing medical and administrative data in a hospital. The hospital information system comprises in particular one or multiple servers which serve to receive and process health data for providing the health data to users, which for example can access the hospital information system internally in the hospital from stationary workstations or using mobile communication devices such as tablet computers or smart phones.

A hospital information system may in particular comprise or serve as a patient data monitoring system (PDMS, commonly used in Europe) or electronic medical record (EMR, commonly used for example in the US), for collecting and processing patient-related information. From a technical viewpoint, EMR refers generally to a permanent database, whereas PDMS refers to a end-user interface displayed at the patient bedside. As an overlying architectural concept, the hospital information system (HIS) provides for a global system architecture for inter-connecting medical devices, PDMS/EMR databases, mobiles communication devices through the hospital network (no matter it is wired or wireless For connecting a server of a hospital information system/patient data monitoring system to a communication network of a healthcare environment, conventionally a statically configured connection is used. Hence, prior to interaction with the communication network, both the server and the network, in particular a gateway for sending outbound health data to the server, must be configured, upon which the server statically remains connected to the network. The configuration typically is carried out by an IT administrator in a manual fashion and may lead to an interruption of services to other systems.

Furthermore, with conventional setups a redundancy scheme for providing a backup in case of failure of a server of a hospital information system may be difficult in that it may increase the data traffic or may require specific, additional network hardware.

It is an object of the instant invention to provide a system and a method for communicating health data in a healthcare environment, which may allow for an easy connection of a consuming device to a network with the possibility to reduce the data load and to improve a backup handling.

This object is achieved by a system for communicating health data in a healthcare environment comprising the features of claim 1.

Accordingly, the consuming device, for receiving health data from the reporting device, is constituted to send a subscription request message containing a subscription request to the reporting device, and the reporting device is constituted, upon receiving the subscription request message, to validate the subscription request and to establish the communication channel to transfer health data to the consuming device.

A communication channel for transferring health data from the reporting device to the consuming device hence may be set up dynamically upon a subscription request by the consuming device. The establishment of the communication channel is initiated by the subscription request message sent from the consuming device to the reporting device, upon which the reporting device validates the subscription request contained in the subscription request message and, upon successful validation, establishes the communication channel to transfer health data to the consuming device.

Because the setup of the communication channel may take place dynamically, no static configuration of the reporting device and the consuming device is required, which may help to reduce efforts for establishing the connection. In particular, no actions by an IT administrator may be required, the establishment of the communication channel taking place automatically by negotiations in between the consuming device and the reporting device.

By means of the subscription request the consuming device indicates that it wishes to receive health data. The subscription request herein may be specific in that it may define a specific group of patient care devices (for example infusion devices) from which health data shall be routinely received, for example patient care devices located in a specific location, for example a specific department of a hospital. Once the communication channel is established, the reporting device will routinely transfer health data as specified according to the subscription request, e.g., health data collected from a specified subset of patient care devices, to the consuming device, which collects the health data and processes the health data for further use for example within a hospital information system.

The consuming device may, in one embodiment, be constituted to send the subscription request message via a secured channel different than the communication channel, for example a channel according to HTTPS. HTTPS stands for Hypertext Transfer Protocol Secure and represents a communication protocol in particular for the Internet for secure transfer of data. An HTTPS connection is in particular secure in that it uses an encryption and authentication. The encryption in particular uses SSL/TLS.

The communication channel which is established upon successful validation of the subscription request contained in the subscription request message may, in one embodiment, use a different technology than the secured channel used for sending the subscription request message. The communication channel may be set up as a secure connection and may in particular use a TCP/IP connection, in particular an MLLP connection. TCP/IP stands for Transmission Control Protocol/Internet Protocol, as it is used in the Internet, the identification of parties of the network taking place by means of IP addresses. MLLP stands for Minimal Lower Layer Protocol. An MLLP connection may in particular be specified by the HL7 group of standards for exchanging health data within a medical environment, in particular in between systems within a hospital communication network or between systems of different hospitals.

In one embodiment, the reporting device is constituted to send, upon receiving the subscription request message, a reply message to the computing consuming device to validate the subscription request. The reply message beneficially is send on the same secure channel on which also the subscription request message is sent, such that the reporting device replies to the consuming device on the same channel. The reply message indicates whether the validation of the subscription request in the subscription request message has been successful. If the subscription request has been validated, the reporting device will open up the communication channel on the communication network using parameters as specified in the subscription request.

In one embodiment, the reporting device may be a so-called device observation reporter (DOR) constituted to receive health data from one or multiple patient care devices located in the healthcare environment. The consuming device, in turn, may be a device observation consumer (DOC) constituted to receive health data from the device observation reporter. A DOR typically serves for collecting health data from patient care devices, including those based on proprietary formats, and is constituted to map and format the collected data to transactions providing a consistent syntax and semantics. A DOC, in turn, serves to receive the heath data of the patient care devices from the DOR, collects the received health data and processes the health data.

The communication between the DOR and the DOC may be defined by so-called integration profiles (for example standardized integration profiles such as IHE IPEC, DEC, ACM or the like), which in particular may define a format and syntax of health data to be transferred from the DOR to the DOC and exchange sequences for transmitting the health data such that the health data may be received and processed within the DOC according to a standardized format and syntax.

In one embodiment, the consuming device is a hospital information system constituted to receive and process the health data and to provide information to users, which may access the hospital information system for example from stationary workstations or using mobile communication devices.

The subscription request contained in the subscription request message may comprise information defining the communication channel to be set up for transferring the health data from the reporting device to the consuming device. In particular, the subscription request may contain information relating to a unique identifier, network connectivity parameters, an integration profile, a refresh delay, and a location in the healthcare environment.

The unique identifier may be used to identify the connection (communication channel) set up in between the reporting device and the consuming device.

Network connectivity parameters may for example include a TCP/IP address, a hostname and a port to be used.

Information relating to an integration profile may relate to a standard integration profile to be used for the communication, such as IHE (IPEC, DEC, ACM or the like), FHIR or a proprietary integration profile.

Information relating to a refresh delay may define a periodicity by which health data shall be refreshed, i.e., a periodicity for sending health data messages relating for example to a specific set of patient care devices such as infusion devices from the reporting device to the consuming device.

Information relating to a location may for example serve to identify a location within the healthcare environment, for example a specific department of a hospital, a specific set of rooms within a department of a hospital or the like, to identify a set of patient care devices from which health data shall be transferred to the consuming device. Generally, a hospital may be organized in a hierarchical, tree-like manner, the top level being defined as the entire hospital, which can be broken down into hierarchical levels relating to departments, rooms (in a department) and beds (in a room). The location information may relate to such hierarchical structure, defining for example a specific department or a specific set of rooms in a department, or a particular bed in a room in a department. According to the subscription, the reporting device hence only sends those health data to the consuming device which relates to the specified set of patient care devices, for example only to those patient care devices located in a specific area of a hospital, for example in a specific department or in a specific bedroom. Hence, not all health data collected within the entire healthcare environment is sent to the consuming device, for example the hospital information system, such that data load on the network is inherently reduced.

The object is also achieved by means of a method for communicating health data in a healthcare environment, the method comprising: transferring health data via a communication channel of a communication network from a reporting device to a consuming device, wherein the consuming device, for receiving health data from the reporting device, sends a subscription request message containing a subscription request to the reporting device, and the reporting device, upon receiving the subscription request message, validates the subscription request and establishes the communication channel to transfer health data to the consuming device.

The advantages and advantageous embodiments described above for the system equally apply also to the method, such that it shall be referred to the above.

The idea underlying the invention shall subsequently be described in more detail with reference to the embodiments shown in the figures. Herein:

FIG. 4 shows a schematic drawing of a healthcare environment having multiple device observation consumers (DOC) interacting with a device observation reporter (DOR).

FIG. 1 shows a schematic drawing of a healthcare environment 1, corresponding for example to the organization of a hospital.

Figure 1:
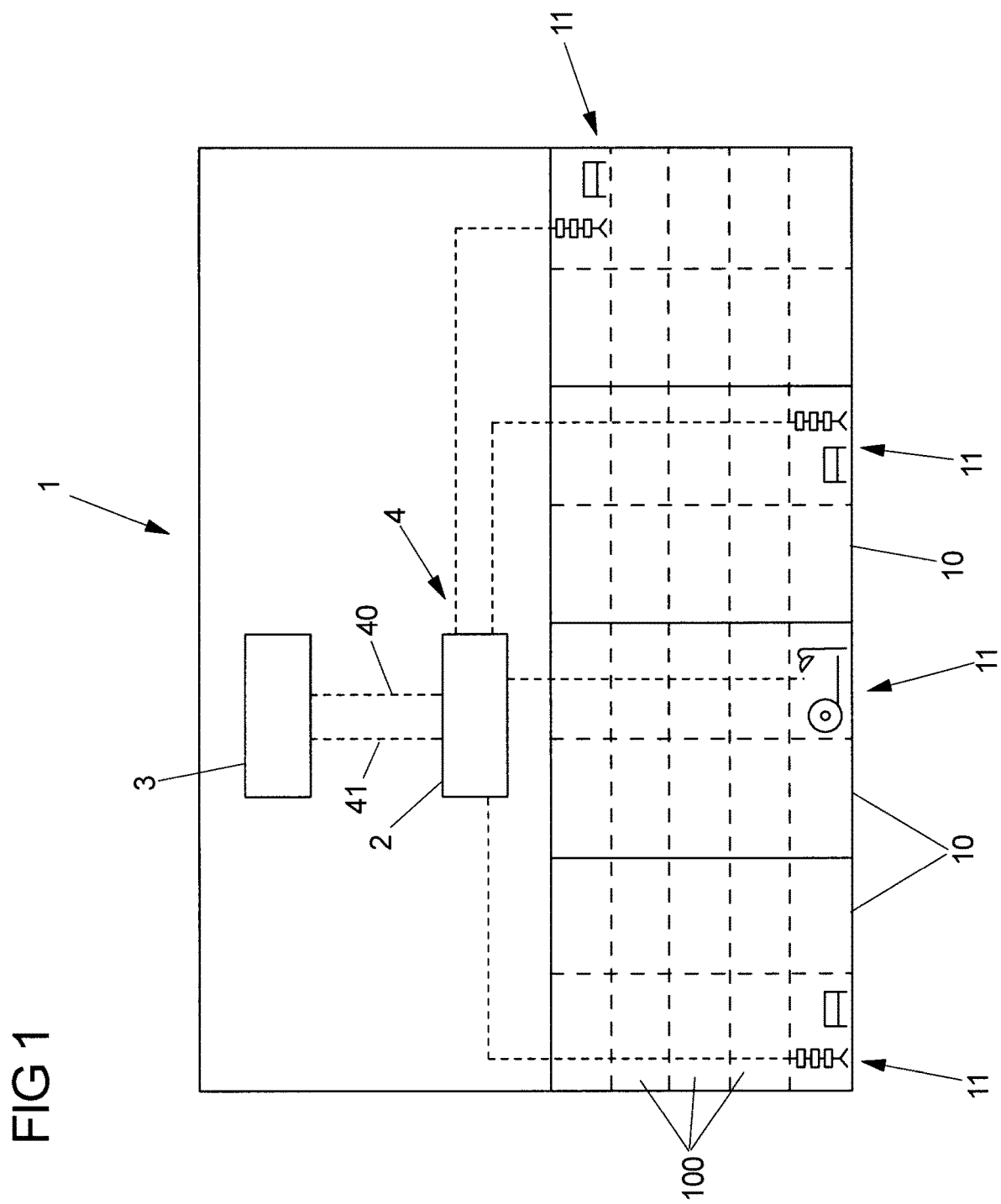
FIG. 1 shows a schematic drawing of a healthcare environment such as a hospital comprising patient care devices connected to a communication network.

The healthcare environment 1 may comprise different departments 10 each having a set of rooms 100 in which patient care devices (in short PCD) such as infusion devices for administering medical fluids to patients may be operated under the attention of medical staff of the different departments 10. The departments 10 may for example correspond to general wards of a hospital, an intensive care unit, an emergency department or specialized departments, e.g., relating to therapeutic services (for example an oncology department or a pharmacy) and diagnostic services (for example a radiology or cardiology department).

The healthcare environment 1 comprises an internal communication network 4 for providing for a data communication in between the different informational systems of the healthcare environment 1. The communication network 4 in particular may comprise a gateway 2 to which the multiplicity of patient care devices 11 are connected and which serves to provide for a data communication to and from the patient care devices 11.

Via the gateway 2 the patient care devices 11 may in particular be connected to a hospital information system 3, which serves to collect, process and distribute health data for informational use within the healthcare environment 1, wherein for example medical staff may access the hospital information system 3 using stationary workstations or mobile computing devices such as a tablet computer or the like to obtain medical information for example relating to a specific patient.

Within the communication network 4, the gateway 2 may in particular serve as a reporting device, in particular a so-called device observation reporter (DOR) for providing health data collected from the patient care devices 11 to the hospital information system 3, which serves as a consuming device, in particular a so-called device observation consumer (DOC). The gateway 2 collects and preprocesses health data, such as operational data and patient data received from the patient care devices 11, in order to for example map and format data received from the patient care devices 11 according to a standardized syntax and semantics for transferring the health data to the hospital information system 3.

The transfer of health data from the gateway 2 to the hospital information system 3, in particular a server of the hospital information system 3, takes place via a communication channel 41. Because a static configuration of the communication channel 41 is cumbersome and involves actions by an IT administrator and furthermore may cause a disruption of services to other devices within the communication network 4, it herein is proposed to use a dynamic registration scheme allowing for a dynamic set-up of the communication channel 41 upon request by a consuming device, in particular a server of the hospital information system 3.

Figure 2:
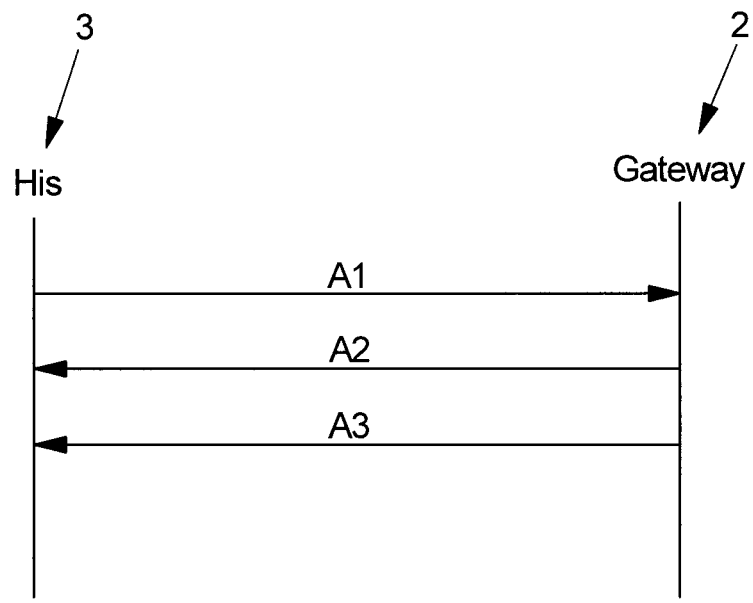
FIG. 2 shows a schematic view of a communication between a consuming device and a reporting device for establishing a communication channel for transferring health data from the reporting device to the consuming device.

In particular, as schematically shown in FIG. 2, for establishing the communication channel 41, it is proposed that a server of the hospital information system 3 (functioning as a consuming device) sends a subscription request message A1 comprising a subscription request, upon which the gateway 2 (functioning as a reporting device) responds by sending a reply message A2. The subscription request message A1 and the reply message A2 both are sent via a secure channel 40, which may for example be set up according to HTTPS. Herein, the message A2 is sent synchronously by the gateway 2, i.e., the hospital information system 3 waits for the response A2 before doing something else.

The subscription request contained in the subscription request message A1 contains information relating to the setup of the desired communication channel 41, in particular a unique identifier, network connectivity parameters such as a TCP/IP address/a hostname and a port of the server of the hospital information system 3 to be connected, a standard integration profile such as IHE IPEC, DEC, ACM or the like to be used for the communication via the communication channel 41, a specific refresh delay parameter and a location in the healthcare environment 1 from which health data shall be collected and transferred to the server of the hospital information system 3. The gateway 2 validates the subscription request and, upon successful validation (which is indicated in the reply message A2), establishes the communication channel 41 to send messages A3 containing health data, such that the server of the hospital information system 3 is connected to the gateway 2 and hence may receive health data collected from a specified group of patient care devices 11 via the gateway 2.

Because the setup of the communication channel 41 takes place automatically by negotiations in between the consuming device (the server of the hospital information system 3) and the reporting device (the gateway 2), the installation of the server within the communication network 4 is easy and does not disrupt any services provided by the gateway 2 to other parties.

The communication channel 41 herein may use a different protocol than the secure channel 40 and may for example be an MLLP channel.

Because, according to the negotiations in between the consuming device and the reporting device in the context of the subscription request, only those health data relating to a specific subset of patient care devices 11—for example only patient care devices 11 located in a specific area within the healthcare environment 1, for example within a specific department 10 or a specific set of rooms 100 of a specific department 10—are send towards the consuming device, data load in the communication network 4 is reduced in that the consuming device will receive only those health data that it has subscribed for.

Furthermore, according to the subscription request a specific refresh delay, i.e., a periodicity of data communication, may be set individually for the established communication channel 41, allowing to further reduce data load because less critical health data may be transferred with a low repetition rate.

In addition, the proposed scheme may improve a backup handling in case of failure of a server of the hospital information system 3.

Figure 3:
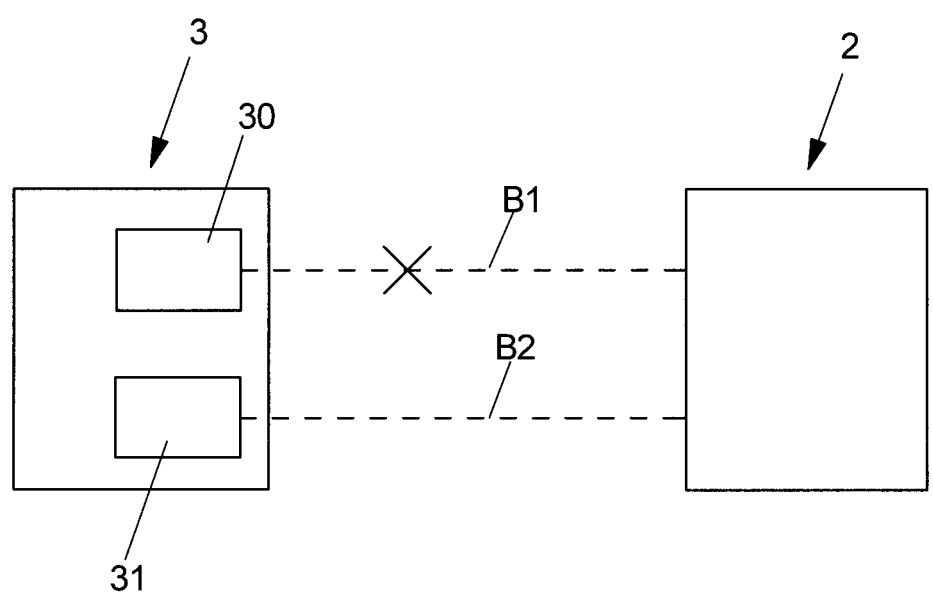
FIG. 3 shows a schematic drawing of a backup handling.

In particular, the hospital information system 3, as schematically indicated in FIG. 3, may comprise redundant servers 30, 31, which may be separate hardware components or may be implemented in software as virtual servers, the one server 30 being the primary server and the other server 31 being a secondary, backup server to take over in case of failure of the primary server 30. For collecting health data from the gateway 2, the primary server 30, during regular operation, sets up a connection B1 according to the scheme described above and in particular using a unique identifier uniquely identifying the connection. In case of failure of the primary server 30, which may be detected within the hospital information system 3 by a suitable failure detection (including for example the exchange of so-called "keep-alive" messages between the servers 30, 31), the secondary server 31 sends a subscription request message A1 (as shown in FIG. 2) to the gateway 2 using the same unique identifier as previously used by the primary server 30. The gateway 2 hence notices that another server 31 using the same unique identifier is scheduled to take over from the primary server 30, upon which the gateway 2 send a reply message A2 to the secondary server 31 and establishes a communication channel B2 to the secondary server 31 for providing the health data according to the identified subscription from now on to the secondary server 31. In case of failure of the primary server 30, hence, a backup server 31 may easily connect to the gateway 2, upon which health data is sent to the secondary server 31 instead of the primary server 30, such that the secondary server 31 seamlessly takes over functionalities from the primary server 30, the server 30, 31 sharing the same database referential, i.e., the backup server 31 receives the same set of data that previously has been sent to the server 30.

FIG. 4 shows a schematic drawing of a setup of a healthcare environment 1 in which multiple device observation consumers (DOC) 3, for example in the shape of a different PDMS/EMR of a hospital information system, communicate with a device observation reporter (DOR) in the shape of a gateway 2 of a communication network 4. Both device observation consumers 3 herein have subscribed to the gateway 2 using the scheme described above according to FIG. 2, in particular by sending an individual subscription request message A1 via a secure channel 40 to the gateway 2, upon which the gateway 2 responds with a reply message A2 and setups communication channels 41 for providing health data to the device observation consumers 3 according to their subscription.

For setting up the subscription, each device observation consumer 3 sends an individual subscription message A1 containing an individual refresh delay parameter, a unique identifier, network connectivity parameters such as an IP address and a port, information relating to an integration profile to be used and locational information identifying the set of patient care devices for which health data shall be provided to the device observation consumer 3.

In the noted example, the device observation consumer 3 on the left has a unique identifier #1, and an IP address/port #1. With the subscription request message A1 the device observation consumer 3 sends a particular refresh delay #1, the unique identifier #1, the IP address/port #1, information with regard to the integration profile #1 to be used and location information A relating to a set of patient care devices located within different rooms of e.g. different wards of the healthcare environment 1, as indicated in FIG. 4.

Likewise, the device observation consumer 3 on the right has a unique identifier #2, and an IP address/port #2. With the subscription request message A1 the device observation consumer 3 sends a particular refresh delay #2, the unique identifier #2, the IP address/port #2, information with regard to the integration profile #2 to be used and location information B relating to a set of patient care devices located within different rooms of e.g. different wards of the healthcare environment 1, as indicated in FIG. 4.

Accordingly, the gateway 2 sets up individual communication channels 41 to each device observation consumer 3 for providing an individual set of health data to the particular device observation consumer 3 according to the specified integration profiles, providing data from patient care devices located within the areas A, B as identified by the location information of the subscription request message A1.

The idea underlying the invention is not limited to the embodiments described above, but may be implemented in an entirely different fashion in entirely different embodiments.

In particular, a subscription scheme as proposed herein may be used in between any reporting device and consuming device within a healthcare environment and is not limited to the specific entities mentioned herein.

A subscription request may comprise additional or different information then noted herein.

Furthermore, the channels may be set up according to different technologies and protocols and are not limited to the protocols mentioned herein.

LIST OF REFERENCE NUMERALS

1 Healthcare environment (hospital)
10 Departments
100 Rooms
11 Patient care devices
2 Reporting entity (gateway)
3 Consuming entity (hospital information system)
30 Primary server
31 Secondary server
4 Hospital communication network
40 Secured channel
41 Communication channel
A1, A2, A3 Messages
B1, B2 Connections

The invention claimed is:

1. A system for communicating health data in a healthcare environment, comprising:
a communication network for communicating health data in the healthcare environment,
a reporting device for transferring health data via the communication network, and
a consuming device for receiving health data from the reporting device via a communication channel of the communication network,
wherein the consuming device is not configured in a manual fashion by an administrator and no static configuration of the consuming device or reporting device is required,
wherein the consuming device, for receiving health data from the reporting device, is configured to initiate upon request of the consuming device the establishment of the communication channel by sending a subscription request message containing a subscription request to the reporting device, the subscription request defining a specific group of patient care devices from which health data shall be routinely received, and the reporting device is configured, upon receiving the subscription request message, to validate the subscription request and establish the communication channel to transfer the health data to the consuming device, the sending of the subscription request message and the validation of the subscription request being an automatic negotiation between the consuming device and the reporting device with no actions required by the administrator,
wherein the specific group of patient care devices comprise fewer than all patient care devices within the healthcare environment, the healthcare environment comprises a plurality of organizational locations, and the specific group of patient care devices is defined by an organizational location of the healthcare environment, and wherein the communication channel is an individual communication channel with a unique identifier, another consuming device being configured to send the unique identifier to the reporting device to establish another communication channel, the another communication channel providing health data according to the subscription request, wherein the subscription request contains information relating to each of the unique identifier, a network connectivity parameter, an integration profile, a refresh delay, and the organizational location of the healthcare environment, and wherein the information relating to the organizational location identifies one or more departments or one or more wards from which health data is to be transferred to the consuming device, the specific group of patient care devices comprising infusion devices.

2. The system according to claim 1, wherein the consuming device is configured to send the subscription request message via a secured channel different than the communication channel.

3. The system according to claim 2, wherein the secured channel is a channel according to Hypertext Transfer Protocol Secure.

4. The system according to claim 1, wherein the communication channel is a channel according to Transmission Control Protocol/Internet Protocol.

5. The system according to claim 4, wherein the communication channel is a channel according to Minimal Lower Layer Protocol.

6. The system according to claim 1, wherein the reporting device is configured to send, upon receiving the subscription request message, a reply message to the consuming device to validate the subscription request.

7. The system according to claim 1, wherein the reporting device is a device observation reporter configured to receive health data from at least one patient care device located in the healthcare environment.

8. The system according to claim 7, wherein the consuming device is a device observation consumer configured to receive health data from the device observation reporter.

9. The system according to claim 1, wherein the consuming device is a first redundant server in a hospital information system, the consuming device being the primary server, and the another consuming device is a second redundant server, the another consuming device being the secondary, backup server, and the another consuming device is configured to send the unique identifier to the reporting device in case of a failure of the primary server.

10. The system according to claim 1, wherein the consuming device is configured to send the subscription request message via a secured channel different than the communication channel, and the reporting device is configured to send a reply message to the consuming device to validate the subscription request via the secured channel.

11. The system according to claim 10, wherein the consuming device waits for the reply message before taking further action.

12. The system according to claim 10, wherein the secured channel is a channel according to Hypertext Transfer Protocol Secure.

13. The system according to claim 10, wherein the communication channel is a channel according to Transmission Control Protocol/Internet Protocol.

14. A method for communicating health data in a healthcare environment, comprising:

transferring health data via a communication channel of a communication network from a reporting device to a consuming device, wherein the consuming device is not configured in a manual fashion by an administrator and no static configuration of the consuming device or reporting device is required, at the consuming device, for receiving health data from the reporting device, initiating upon request of the consuming device the establishment of the communication channel by sending a subscription request message containing a subscription request to the reporting device, the subscription request defining a specific group of patient care devices from which health data shall be routinely received, wherein the specific group of patient care devices comprise fewer than all patient care devices within the healthcare environment, the healthcare environment comprises a plurality of organizational locations, and the specific group of patient care devices is defined by an organizational location of the healthcare environment, and at the reporting device, upon receiving the subscription request message, validating the subscription request and establishing the communication channel to transfer the health data to the consuming device, the sending of the subscription request message and the validating of the subscription request being an automatic negotiation between the consuming device and the reporting device with no actions required by the administrator, and wherein the communication channel is an individual communication channel with a unique identifier, and, at another consuming device, sending the unique identifier to the reporting device to establish another communication channel, the another communication channel providing health data according to the subscription request, wherein the subscription request contains information relating to each of the unique identifier, a network connectivity parameter, an integration profile, a refresh delay, and the organizational location of the healthcare environment, and wherein the information relating to the organizational location identifies one or more departments or one or more wards from which health data is to be transferred to the consuming device, the specific group of patient care devices comprising infusion devices.

15. The method according to claim 14, wherein the consuming device is configured to send the subscription request message via a secured channel different than the communication channel, and the reporting device is configured to send a reply message to the consuming device to validate the subscription request via the secured channel.

16. The method according to claim 15, wherein the consuming device waits for the reply message before taking further action.

17. The method according to claim 15, wherein the secured channel is a channel according to Hypertext Transfer Protocol Secure.

18. The method according to claim 15, wherein the communication channel is a channel according to Transmission Control Protocol/Internet Protocol.

* * * * *